(12) United States Patent
Jiang et al.

(10) Patent No.: US 7,722,809 B2
(45) Date of Patent: May 25, 2010

(54) BIOAGENT DETECTION DEVICE

(75) Inventors: Hongrui Jiang, Madison, WI (US);
David J. Beebe, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1391 days.

(21) Appl. No.: 11/144,723

(22) Filed: Jun. 3, 2005

(65) Prior Publication Data

US 2006/0078462 A1   Apr. 13, 2006

Related U.S. Application Data

(60) Provisional application No. 60/576,989, filed on Jun. 4, 2004.

(51) Int. Cl.
| | |
|---|---|
| G01N 21/00 | (2006.01) |
| G01N 33/53 | (2006.01) |
| G01N 11/00 | (2006.01) |
| F16K 31/12 | (2006.01) |
| F17D 1/16 | (2006.01) |
| G01N 21/77 | (2006.01) |
| E03B 1/00 | (2006.01) |

(52) U.S. Cl. .............................. 422/58; 422/63; 435/7.1; 73/53.01; 251/12; 137/14; 137/3; 436/169

(58) Field of Classification Search .................. 422/58, 422/63; 435/7.1; 73/53.01; 251/12; 137/14, 137/3; 436/169
See application file for complete search history.

(56) References Cited

U.S. PATENT DOCUMENTS

| | | | | |
|---|---|---|---|---|
| 6,491,061 | B1 * | 12/2002 | Lopez et al. | 137/599.01 |
| 6,523,559 | B2 * | 2/2003 | Beebe et al. | 137/3 |
| 6,990,849 | B2 * | 1/2006 | Bohm et al. | 73/53.01 |
| 7,111,635 | B2 * | 9/2006 | Beebe et al. | 137/14 |
| 2003/0096310 | A1 * | 5/2003 | Hansen et al. | 435/7.1 |
| 2006/0090800 | A1 * | 5/2006 | Banerjee et al. | 137/827 |
| 2006/0093528 | A1 * | 5/2006 | Banerjee et al. | 422/103 |
| 2008/0069729 | A1 * | 3/2008 | McNeely | 422/63 |

OTHER PUBLICATIONS

Beebe et al., Functional hydrogel structures for autonomous flow control inside microfluidic channels, 2000, Nature, v. 404, p. 588-590.*

* cited by examiner

*Primary Examiner*—Lore Jarrett
(74) *Attorney, Agent, or Firm*—Boyle Fredrickson, S.C.

(57) ABSTRACT

A detection device is provided for detecting the presence of an agent in a fluid. The device includes a body defining first and second chambers. It is intended for the first chamber accommodating the flow of fluid therein. A first valve is disposed in the body between in the first and second chambers. The first valve opens in response to the presence of the agent in the fluid. A first detection structure is disposed in the second chamber in order to generate a predetermined signal in response to exposure to the fluid.

20 Claims, 2 Drawing Sheets

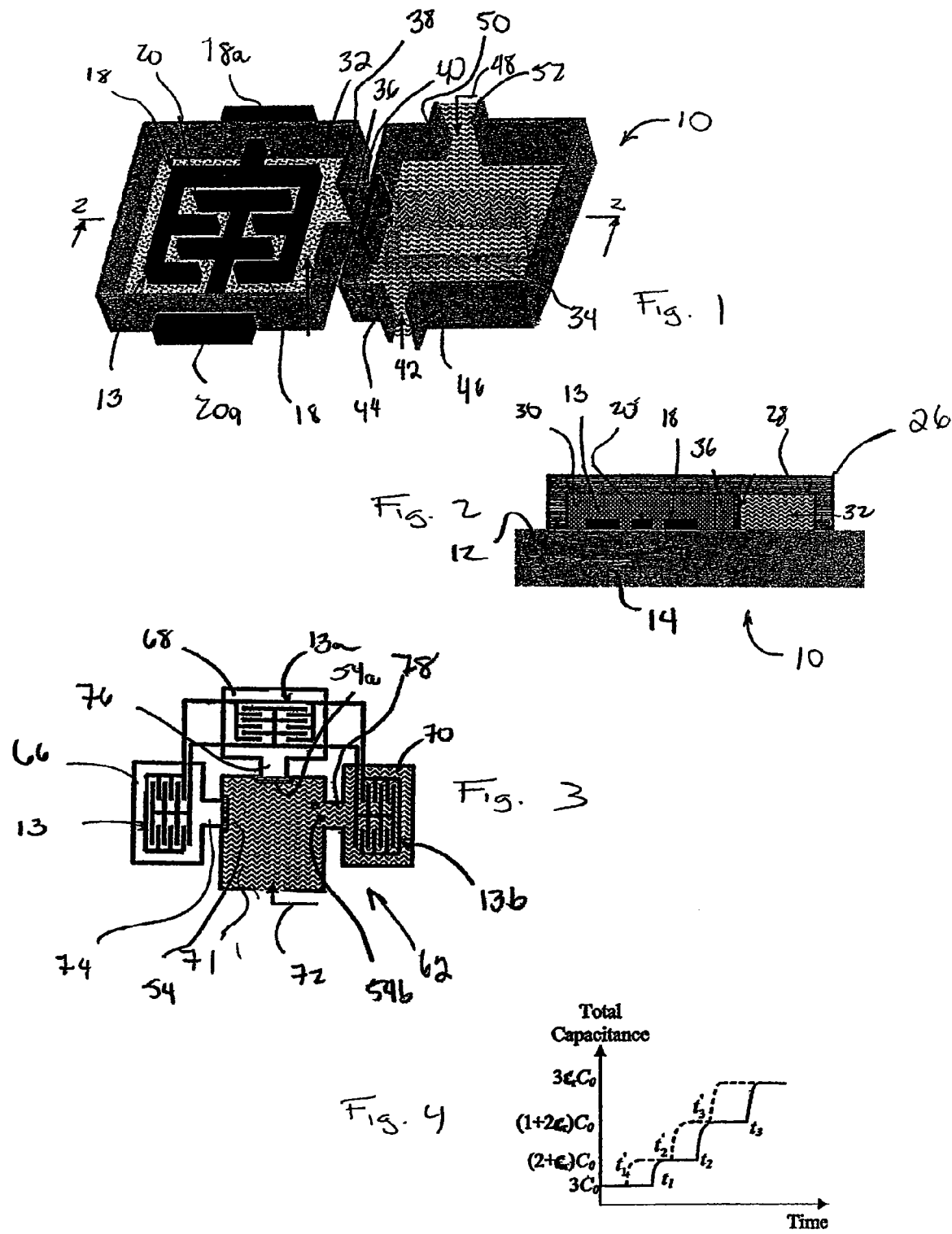

BIOAGENT DETECTION DEVICE

CROSS-REFERENCE TO RELATED APPLICATION

Figure 5:
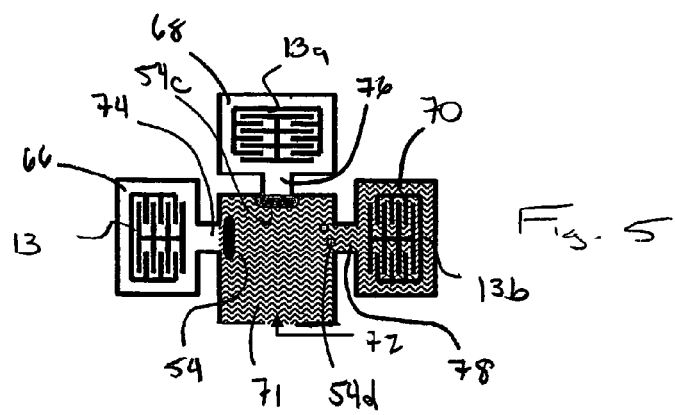

This application claims the benefit of U.S. Provisional Application Ser. No. 60/576,989, filed Jun. 4, 2004.

REFERENCE TO GOVERNMENT GRANT

This invention was made with United States government support awarded by the following agencies: DOD/ARPA F30602-00-2-0570. The United States has certain rights in this invention.

FIELD OF THE INVENTION

This invention relates generally to bioagent detection systems, and in particular, to a real time, bioagent detection device that incorporates a microsensor for sensing bioagents in both the air and aqueous environments.

BACKGROUND AND SUMMARY OF THE INVENTION

Potential biological attacks against large scale civilian populations have become an important issue in homeland security. By way of example, the anthrax cases in the United States in 2001 and the ricin case on Capitol Hill in 2004 have proven that the threat of a biological attack is real. In order to thwart any potential biological attack, the development of a civilian biodefense plan is crucial. Consequently, there has been an enormous effort to develop practical and efficient biosensors in recent years.

Most present biosensors take advantage of biologically active materials for high sensitivity and selectivity. In general, the biosensor includes a biorecognition structure (e.g., a membrane) in contact with or interrogated by a transducer. The biologically active material recognizes a particular biological molecule through a reaction, specific adsorption, or other physical or chemical process, and the transducer converts the output of this recognition into a usable signal, usually electrical or optical. Many approaches have been explored to achieve ultra-sensitive detection of bio-species. These biodetection approaches can be categorized as either an engineering-oriented approach or a biological-oriented approach. In other words, most biodetection schemes are either based on relatively complex electronic, photonic and/or electrochemical methods or more elegant biomolecular methods (e.g. enzyme linked immunosorbent assay, or ELISA) typically with an optical or spectrometry-based readout.

By way of example, one process utilizes photonics integrated on a microchip to study the interaction between the optical field and the target bio-analyte. Because most biorecognition processes occur in an aqueous ambient, this approach requires the integration of photonics, highly sensitive microelectronics and microfluidic systems on a single microchip. The use of ion-channel switches as biosensors has also been explored, but the bioelectronic interface is a delicate one. Often, when an approach promises very high sensitivity, the output signal from the biorecognition is very small, thus requiring extremely highly-sensitive on-chip microelectronics for signal amplification, processing and wireless transmission. The high demand of these approaches on system integration and high sensitivity photonics and electronics circuitry presents a big challenge to the biosensors in terms of cost, reliability and power consumption. The more biomolecular based approaches, like ELISA, are simple, but typically require a macro scale spectrometry system to quantify the output.

Therefore, it is a primary object and feature of the present invention to provide a bioagent detection device that is highly sensitive and selective, has a quick response time (on the order of one hour or less) and generates few false alarms.

It is a further object and feature of the present invention to provide a bioagent detection device that is small in size and weight and is inexpensive to manufacture.

It is a still further object and feature of the present invention to provide a bioagent detection device that possesses wireless communication capability over a large area span.

It is a still further object and feature of the present invention to provide a bioagent detection device that is able to operate in different environments, such as in air and in water, without premature failure.

In accordance with the present invention, a detection device is provided for detecting the presence of a bioagent in a fluid. The detection device includes a body defining a first chamber for accommodating the fluid therein and a second chamber. A detection structure is disposed in the second chamber of the body. The detection structure generates a predetermined signal in response to exposure to the fluid. A valve interconnects the first and second chambers. The valve opens in response to the presence of the bioagent in the fluid in the second chamber.

The valve may be fabricated from a polymeric material that dissolves in response to exposure to the bioagent. The detection structure may include a microcapacitor having first and second terminals for connecting the detection structure to a signal detection circuit, as well as, first and second spaced electrodes. With the valve open, fluid flows into the second chamber. The microcapacitor has a first capacitance in the absence of fluid in the second chamber and a second capacitance with the fluid in the second chamber. The body may also define a channel having an input communicating with the first chamber and an output communicating with the second chamber. The valve includes a dissolvable member in the first chamber overlapping the input to the channel.

The body may also define a third chamber. A second detection structure may be disposed in the third chamber of the body. The second detection structure generates a predetermined signal in response to exposure to the fluid. A second valve interconnects the first and third chambers. The second valve opens in response to the presence of a second bioagent in the fluid in the first chamber. Alternatively, the second valve may open in response to the presence of the bioagent in the fluid in the first chamber. It is contemplated for the first valve to open a first predetermined time period after exposure to the bioagent and the second valve to open a second predetermined time period after exposure to the bioagent and for the first predetermined time period to be less than the second predetermined time period.

In accordance with a further aspect of the present invention, a detection device is provided for detecting the presence of a bioagent in a fluid. The detection device includes a body defining a first chamber for accommodating the fluid therein and a second chamber. A first valve is disposed in the body. The first valve has a first closed configuration wherein the first and second chambers are isolated and a second open configuration wherein the first and second chambers communicate. A first detection structure is disposed in the second chamber. The first detection structure generates a predetermined signal in response to exposure to the fluid.

The body further defines a channel extending between the first and second chambers. The channel has an input communicating with the first chamber and an output communication with the second chamber. The first valve overlaps the input to the channel. The first valve includes a polymeric material isolating the first and second chambers. The polymeric material dissolves in response to exposure to the bioagent.

The detection structure includes a microcapacitor having first and second terminals for connecting the detection structure to a signal detection circuit. The second chamber accommodates the flow of fluid therein with the valve in the open configuration. The microcapacitor has a first capacitance in the absence of fluid in the second chamber and a second capacitance with the fluid in the second chamber.

The body may also define a third chamber. A second valve is disposed in the body. The second valve has a first closed configuration wherein the first and third chambers are isolated and a second open configuration wherein the first and third chambers communicate. A second detection structure is disposed in the third chamber for generating a predetermined signal in response to exposure to the fluid.

The first valve is formed from a first polymeric material that isolates the first and second chambers. The first polymeric material dissolves in response to exposure to a first bioagent. However, the second valve may be formed from a second polymeric material that isolates the first and third chambers. The second polymeric material dissolves in response to exposure to a second bioagent.

It is contemplated for the first valve to open a first predetermined time period after exposure to the bioagent and for the second valve to open a second predetermined time period after exposure to the bioagent. The first predetermined time period is less than the second predetermined time period.

In accordance with a still further aspect of the present invention, a method is provided for detecting the presence of a bioagent in a fluid. The method includes the step of passing the fluid into a body defining first and second chambers. The first and second chambers are isolated from each other by a first valve. The first valve opens in response to the bioagent in the fluid so as to allow fluid to flow into the second chamber. A signal is generated in response to the presence of fluid in the second chamber.

The first valve is formed from a polymeric material that dissolves in response to exposure to the bioagent and the step of generating the signal includes the additional step of providing a microcapacitor having an initial capacitance in the second chamber. The capacitance of the microcapacitor is varied in response to the presence of fluid in the second chamber and the change in capacitance is detected. The method of the present invention may also include the additional steps of providing a third chamber in the body and opening a second valve in response to a second bioagent in the fluid so as to allow fluid to flow into the third chamber. Thereafter, a second signal is generated in response to the presence of fluid in the third chamber. Alternatively, the second valve is opened in response to the bioagent in the fluid so as to allow fluid to flow into the third chamber. Thereafter, the signal is varied in response to the presence of fluid in the third chamber.

The first valve may be formed from a first polymeric material that isolates the first and second chambers. The first polymeric material dissolves in a first predetermined time period in response to exposure to the bioagent. In addition, the second valve may be formed from a second polymeric material that isolates the first and third chambers. The second polymeric material dissolves in a second predetermined time period in response to exposure to the bioagent.

BRIEF DESCRIPTION OF THE DRAWINGS

The drawings furnished herewith illustrate a preferred methodology of the present invention in which the above advantages and features are clearly disclosed as well as others which will be readily understood from the following description of the illustrated embodiment.

In the drawings:

FIG. 1 is a schematic view of a bioagent detection system in accordance with the present invention;

FIG. 2 is a cross-sectional view of the bioagent detection system of the present invention taken along line 2-2 of FIG. 1;

FIG. 3 is a schematic, top plan view of an alternate embodiment of a bioagent detection system in accordance with the present invention;

FIG. 4 is a graphical representation of the capacitance over time of the bioagent detection system of FIG. 3 during operation;

FIG. 5 is a schematic, top plan view of a still further embodiment of a bioagent detection system in accordance with the present invention; and FIG. 6 is a schematic view of a bioagent detection system in accordance with the present invention.

DETAILED DESCRIPTION OF THE DRAWINGS

Referring to FIGS. 1-2, a detection device fabricated in accordance with a methodology as hereinafter described is generally designated by the reference numeral 10. Referring to FIGS. 1, in order to fabricate detection device 10, microcapacitor 13 is fabricated on upper surface 12 of substrate 14. It is contemplated for substrate 14 to take any of a variety of forms, including but not limited to, a silicon wafer, a print circuited board or a sheet of glass. By way of example, microcapacitor 13 may take the form of a surface micromachined, parallel-plate, tunable capacitor that is fabricated on upper surface 12 of substrate 14 with polysilicon and metallized with copper (Cu) through electroless Cu plating. Alternatively, microcapacitor 13 may take the form of a bulk-micromachined, tunable capacitor that is fabricated on upper surface 12 of substrate 14 with bulk single-crystal silicon and metallized with electroless Cu plating.

Microcapacitor 13 includes first and second "comb"-shaped electrodes 18 and 20, respectively, extending perpendicularly from upper surface 12 of substrate 14 and being formed through the electroplating of a metal, such as nickel (Ni). Electrodes 18 and 20 include corresponding connection pads 18*a* and 20*a*, respectively, extending therefrom. Connection pads 18*a* and 20*a*, in turn, are operatively connected to integrated circuit (IC) module 25 at nodes 21 and 23, respectively, FIG. 6. The interconnect between connection pads 18*a* and 20*a* of microcapacitor 13 and IC module 25 can be formed during the electroplating step heretofore described, or alternatively, by wire bonding. The configuration of electrodes 18 and 20 is designed to increase the overlapping areas between the two electrodes. By way of a example, for a 0.75 millimeter×0.75 millimeter capacitor, the initial capacitance with air gap is about 5 picofarads (pF), assuming a width of 5 micrometers and a height of 30 micrometers for electrodes 18 and 20 and a gap of 3 micrometers between electrodes 18 and 20. For reasons hereinafter described, the capacitance of microcapacitor 13 needs to be at least one order of magnitude higher than the parasitic capacitance of the microcapacitor due to the interconnect in order to reduce the substrate noise and the influence of the parasitic capacitance on the total capacitance. Assuming the dielectric material between the metal interconnect and the silicon substrate is 5 micrometers of silicon-oxide, the parasitic capacitance due to the interconnect is 7 aF/$\mu m^2$. A 5 mm long, 10 $\mu m$ wide interconnect would have a total parasitic capacitance of 0.35 pF. Hence, the initial capacitance of microcapacitor 13 should be chosen as at least a few picofarads.

Detection device 10 further includes cartridge 26 formed from a polycarbonate material and having upper and lower surfaces 28 and 30, respectively, interconnected by first and second ends, respectively, and first and second sides, respectively. A plurality of fill holes extend through cartridge 26 and communicate with upper and lower surfaces 28 and 30, respectively, thereof. Cartridge 26 is spaced from upper, surface 12 of substrate 14 by a gasket, two-sided tape or other similar structure so as to define a cavity between lower surface 30 of cartridge 26 and upper surface 12 of substrate 14 for receiving a polymerizable material therein. The polymerizable material is injected into the cavity through any one of the openings through the cartridge 26. An optical mask is affixed to upper surface 28 of cartridge 26. It is intended that the optical mask correspond to the desired shape of any channel network and/or chambers to be formed in the cavity, as hereinafter described.

With the cavity filled with polymerizable material, ultraviolet light, generated by a UV source, is directed towards detection device 10 at an angle generally perpendicular to upper surface 28 of cartridge 26. As is known, the polymerizable material polymerizes and solidifies when exposed to ultraviolet light. It can be appreciated that the optical mask shields a first portion of the polymerizable material from the ultraviolet light. As a result, a second portion of the polymerizable material, which is exposed to ultraviolet light, polymerizes and solidifies. On the other hand, the first portion of polymerizable material, which is not exposed to ultraviolet light, does not polymerize and remains in a fluidic state.

After polymerization of the second portion of material by the ultraviolet light, the optical mask is removed from upper surface 28 of cartridge 26. In addition, the non-polymerized portion of the polymerizable material is flushed from the cavity between lower surface 30 of cartridge 26 and upper surface 12 of substrate 14 using ethanol. It can be appreciated that in the depicted embodiment, the polymerized material defines first and second chambers 32 and 34, respectively, interconnected by flow channel 36. Flow channel 36 has an output 38 communicating with first chamber 32 and an input 40 communicating with second chamber 34. In addition, the polymerized material defines input channel 42 having an input 44 connected to a fluid source and an output 46 communicating with second chamber 34 and output channel 48 having an input 50 communicating with second chamber 34 and an output 52. Output channel 48 may be used to drain fluid from second chamber 34, if so desired. It can be appreciated that the chambers and channel networks formed in detection device 10 may have different configurations without deviating from the scope in the present invention. Further, for reasons hereinafter described, it is noted that the height of the first chamber 32 in detection device 10 greater than the height of electrodes 18 and 20.

Once the chambers and channels are formed in detection device 10, it is contemplated to construct a "valve" across input 40 of flow channel 36 in the form of membrane 54. Membrane 54 is fabricated via interfacial polymerization of a polymeric material directly within second chamber 34 of detection device 10. More specifically, the polymeric material is injected into second chamber 34 and an optical mask is affixed to upper surface 28 of cartridge 26. It is intended that the optical mask include an opening therethrough that corresponds in size and location to a desired pattern for membrane 54. Ultraviolet light is directed towards detection device 10 at an angle generally perpendicular to upper surface 28 of cartridge 26 such that a first portion of the polymeric material polymerizes and forms membrane 54. Thereafter, the non-polymerized portion of the polymeric material that was shielded from the ultraviolet light by the optical mask is flushed from second chamber 34 of detection device 10. As described, membrane 54 overlaps input 40 to flow channel 36 and isolates first chamber 32 from second chamber 34.

It is contemplated for the polymeric material used to fabricate membrane 54 to incorporate peptide sequences that serve as recognition elements for the bioagent to be detected. It is noted that the peptide sequences can serves as recognition elements for other types of agents, such as chemical agents, without deviating from the scope of the present invention. The peptide sequences provide a molecular basis for sensor specificity, as well as, the mechanism by which membrane 54 erodes (i.e., peptide bond cleavage) when exposed to the predetermined bioagent. It can be appreciated that a membrane acting as biological sensor possesses several advantages within a microfluidic platform. For example, small amounts of reagents are needed to produce these membranes. Further, these membranes are thin, lowering the diffusion path length of the agent to be detected (i.e. large enzymes, toxins and proteases).

The operation of detection device 10 is dependant upon a change in the capacitances of microcapacitor 13 that is brought about by the dissolution of membrane 54. As heretofore described, electrodes 18 and 20 of microcapacitor 13 are separated by an air gap. In addition, first chamber 32 is isolated from second chamber 34 by membrane 54. Input channel 42 is connected to a fluid source via an upstream microfluidic system. The microfluidic system generates a sample of fluid and prepares it for deposit in second chamber 34. It is contemplated for the fluid to be a dielectric material having a high relative permittivity, $\epsilon_r$. A small amount of fluid is sampled into second chamber 34. In the absence of the bioagent in the fluid, membrane 54 acts to prevent the fluid from flowing into first chamber 32 though flow channel 36. Alternatively, if a predetermined amount of the bioagent is sampled into second chamber 34, the bioagent will cleave the peptide sequences, thereby causing membrane 54 to become porous and/or dissolve. As a result, the "valve" opens so as to allow the fluid in second chamber 34 to flow into first chamber 32 through flow channel 36. It is contemplated to chemically treat the bottom surfaces of first chamber 32 and flow channel 36 to be hydrophilic so as to facilitate the flow of the fluid into first chamber 32. It can be appreciated that with fluid in first chamber 32 increases the capacitance of microcapacitor 13 by a factor of $\epsilon_r$, the relative permittivity of the dielectric fluid. The large change of capacitance of microcapacitor 13 is detected by IC module 25 that, in turn, generates a positive signal to a user advising them of the presence of the bioagent in the fluid.

Figure 6:
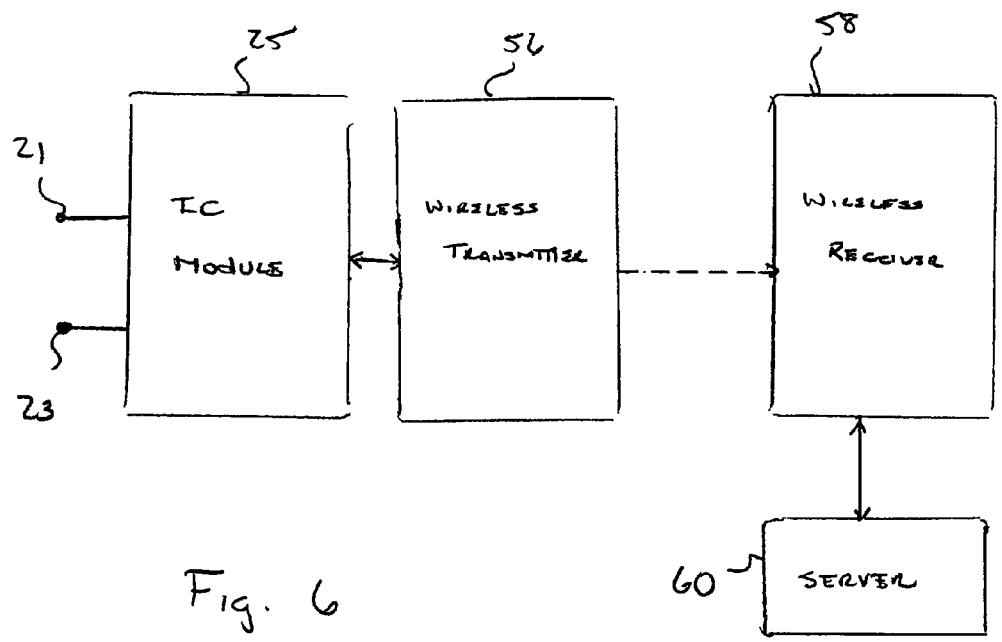

Referring to FIG. 6, with more complicated microcapacitor circuits, hereinafter described, and/or IC module designs, it is contemplated for information to be transmitted wirelessly via wireless transmitter 56 to wireless receiver 58. The information may then be provided to server 60 which can process the information in a desired manner. The targeted frequency range for wireless transmission is between 100 Mhz and 1 GHz. Depending on the transmission power, the transmission distance can vary from tens of meters to miles. In addition, water is almost totally transparent for electromagnetic waves in this frequency range. This, in turn, allows detection device 10 to operate and transmit signals in aqueous environments.

Referring to FIG. 3, an alternate embodiment of the detection device of the present invention is generally designated by the reference numeral 62. It can be appreciated that detection device 62 may be fabricated using the methodology heretofore described with respect to the fabrication of detection device 10. Detection device 62 includes first, second and third capacitor chambers 66, 68 and 70, respectively, adapted for receiving microcapacitors 13, 13a and 13b. Microcapacitors 13, 13a and 13b are identical in structure, and as such, the previous description of microcapacitor 13 is understood to describe microcapacitors 13a and 13b as if fully described herein. Microcapacitors 13, 13a and 13b are connected in parallel to each other in a conventional manner and to IC module 25.

Detection device 62 further defines sample chamber 71 having an input 72 connected to a fluid source via an upstream microfluidic system. The microfluidic system generates a sample of fluid and prepares it for deposit in sample chamber 71. Sample chamber 71 communicates with first, second and third chambers 66, 68 and 70, respectively, through corresponding flow channels 74, 76 and 78, respectively. Each flow channel 74, 76 and 78 has an output communicating with a corresponding first, second and third chamber 66, 68 and 70, respectively and an input communicating with sample chamber 71. Membranes 54, 54a and 54b are disposed in sample chamber 71 so as to overlap the inputs of corresponding flow channels 74, 76 and 78, respectively. Membranes 54a and 54b are identical in structure to membrane 54 but for the concentrations of peptide sequences. As described, it is intended for membranes 54, 54a and 54b to erode (i.e., peptide bond cleavage) at different rates when exposed to the predetermined bioagent. Therefore, it can be appreciated that change of capacitance of microcapacitors 13, 13a and 13b will have a characteristic time response dependant upon the concentration of the bioagent in the fluid. As seen in FIG. 4, by tracking the capacitance change in the time domain, information on the concentration of the bioagent in the sample of fluid can be recovered.

As heretofore described, electrodes 18 and 20 of microcapacitors 13, 13a and 13b are separated by air gaps, and first, second and third chambers 66, 68 and 70 are isolated from sample chamber 71. A small amount of fluid is sampled into sample chamber 71. In the absence of the bioagent in the fluid, membranes 54, 54a and 54b act to prevent the fluid from flowing into first, second and third chambers 66, 68 and 70, respectively, through flow channels 74, 76 and 78, respectively. If a predetermined amount of the bioagent is sampled into sample chamber 71, the bioagent will initially cleave the peptide sequences in membrane 54b, thereby causing membrane 54b to become porous and/or dissolve as depicted in FIG. 3. As a result, the "valve" opens so as to allow the fluid in sample chamber 71 to flow into third chamber 70 through flow channel 78. Thereafter, the bioagent will sequentially cleave the peptide sequences in membranes 54a and 54, thereby causing membranes 54a and 54 to sequentially become porous and/or dissolve. As a result, the "valves" sequentially open so as to allow the fluid in sample chamber 71 to flow into second chamber 68 and, after a predetermined time period into first chamber 66. It is contemplated to chemically treat the bottom surfaces of first, second and third chambers 66, 68 and 70, respectively, and flow channels 74, 76 and 78 to be hydrophilic so as to facilitate the flow of the fluid into first, second and third chambers 66, 68 and 70, respectively. Referring to FIG. 4, it can be appreciated that with fluid sequentially flowing into third, second and first chambers 70, 68 and 66, respectively, increases the capacitance of microcapacitors 13, 13a and 13b connected in parallel over time due to the relative permittivity of the dielectric fluid, $\epsilon_r$. By tracking the capacitance change in the time domain, information on the concentration of the bioagent in the sample of fluid can be recovered.

Referring to FIG. 5, a still further embodiment of the detection device of the present invention is generally designated by the reference numeral 82. Detection device 82 is identical in structure to detection device 62, except as hereinafter provided. As such, the description of detection device 62 is understood to described detection device 82 with the following noted exceptions.

Unlike detection device 62, microcapacitors 13, 13a and 13b are connected directly to IC module 25 in order to allow IC module 25 to determine if the capacitance of an individual microcapacitor 13, 13a and 13b has increased. In addition, membranes 54, 54c and 54d are disposed in sample chamber 71 so as to overlap the inputs of corresponding flow channels 74, 76 and 78, respectively. Membranes 54c and 54d are identical in structure to membrane 54 but for the types of peptide sequences provided therein. It is intended that the peptide sequences in membranes 54, 54c and 54d serve as recognition elements for distinct bioagents to be detected. As such, it is intended that membranes 54, 54c and 54d erode (i.e., peptide bond cleavage) when exposed to the predetermined, corresponding bioagents.

As heretofore described, electrodes 18 and 20 of microcapacitors 13, 13a and 13b are separated by air gaps, and first, second and third chambers 66, 68 and 70 are isolated from sample chamber 71. A small amount of fluid is sampled into sample chamber 71. In the absence of the predetermined bioagents in the fluid, membranes 54, 54c and 54d act to prevent the fluid from flowing into first, second and third chambers 66, 68 and 70, respectively, through flow channels 74, 76 and 78, respectively. If a predetermined amount of a first bioagent is sampled into sample chamber 71, the first bioagent will cleave the peptide sequences in membrane 54d, thereby causing membrane 54d to become porous and/or dissolve, as depicted in FIG. 5. As a result, the "valve" opens so as to allow the fluid in sample chamber 71 to flow into third chamber 70 through flow channel 78. It can be appreciated that with fluid in third chamber 78 increases the capacitance of microcapacitor 13 a predetermined factor of $\epsilon_r$, the relative permittivity of the dielectric fluid. The large change of capacitance of microcapacitor 13b is detected by IC module 25 that, in turn, generates a positive signal to a user advising them of the presence of the first bioagent in the fluid.

Alternatively, if a predetermined amount of a second bioagent is sampled into sample chamber 71, the second bioagent will cleave the peptide sequences in membrane 54c, thereby causing membrane 54c to become porous and/or dissolve. As a result, the "valve" opens so as to allow the fluid in sample chamber 71 to flow into second chamber 68 through flow channel 76. It can be appreciated that the fluid in second chamber 76 increases the capacitance of microcapacitor 13a a predetermined factor of $\epsilon_r$, the relative permittivity of the dielectric fluid. The large change of capacitance of microcapacitor 13a is detected by IC module 25 that, in turn, generates a positive signal to a user advising them of the presence of the second bioagent in the fluid.

Similarly, if a predetermined amount of a third bioagent is sampled into sample chamber 71, the third bioagent will cleave the peptide sequences in membrane 54, thereby causing membrane 54 to become porous and/or dissolve. As a result, the "valve" opens so as to allow the fluid in sample chamber 71 to flow into first chamber 66 through flow channel 74. It can be appreciated that the fluid in first chamber 66 increases the capacitance of microcapacitor 13 a predetermined factor of Cr, the relative permittivity of the dielectric fluid. The large change of capacitance of microcapacitor 13 is detected by IC module 25 that, in turn, generates a positive signal to a user advising them of the presence of the third bioagent in the fluid.

It is noted that in order to continuously monitor air, capture particles and efficiently move the particles into the detection devices of the present invention, the concept of "virtual walls" will be exploited. Utilizing virtual walls technology, the surface energies within a microchannel can be controlled so that a fluid stream is confined to the center of the channel while maintaining gas streams on both sides, creating very large surface area liquid-gas interfaces. Airborne particles flowing through the gas regions and coming into contact with the liquid walls are elegantly transferred from the gas to liquid. Once in the liquid microfluidic environment, the particles can be seamlessly transported to down stream to the detection devices heretofore described. In addition, evaporative effects can be used to concentrate the sample prior to sensing, further enhancing sensitivity.

Various modes of carrying out the invention are contemplated as being within the scope of the following claims particularly pointing out and distinctly claiming the subject matter that is regarded as the invention.

We claim:

1. A detection device for detecting the presence of a bioagent in a fluid, comprising:
- a body defining a first chamber for accommodating fluid therein and a second chamber;
- a detection structure disposed in the second chamber of the body, the detection structure generating a predetermined signal in response to exposure to the fluid, wherein the detection structure includes a microcapacitor having first and second terminals for connecting the detection structure to a signal detection circuit; and
- a valve interconnecting the first and second chambers, the valve dissolving and becoming a solute in the fluid in response to the presence of the bioagent in the fluid in the second chamber, wherein the valve is a membrane material comprising peptide sequences to serve as recogini-tion elements for the bioagent to be detected.

2. The device of claim 1 wherein the microcapacitor includes first and second spaced electrodes.

3. The device of claim 1 wherein fluid flows into the second chamber with the valve dissolved and wherein the microcapacitor has a first capacitance in the absence of fluid in the second chamber and a second capacitance with the fluid in the second chamber.

4. The device of claim 1 wherein the body defines a channel having an input communicating with the first chamber and an output communicating with the second chamber and wherein the valve includes a dissolvable member in the first chamber overlapping the input to the channel.

5. The device of claim 1 wherein the body defines a third chamber and wherein the device further comprises:
- a second detection structure disposed in the third chamber of the body, the detection structure generating a predetermined signal in response to exposure to the fluid; and
- a second valve interconnecting the second and third chambers, the second valve opening in response to the presence of a second bioagent in the fluid in the second chamber.

6. The device of claim 1 wherein the body defines a third chamber and wherein the device further comprises:
- a second detection structure disposed in the third chamber of the body, the detection structure generating a predetermined signal in response to exposure to the fluid; and
- a second valve interconnecting the second and third chambers, the second valve opening in response to the presence of the bioagent in the fluid in the second chamber.

7. The device of claim 6 wherein the first valve opens a first predetermined time period after exposure to the bioagent and the second valve opens a second predetermined time period after exposure to the bioagent and wherein the first predetermined time period is less than the second predetermined time period.

8. The device of claim 6 wherein the first and second detection structures are connected in parallel.

9. A detection device for detecting the presence of a bioagent in a fluid, comprising:
- a body defining first and second chambers, the first chamber accommodating the flow of fluid therein;
- a first valve disposed in the body, the first valve:
  - having a first closed configuration wherein the first and second chambers are isolated and a second open configuration wherein the first and second chambers communicate; and
  - including a polymeric material isolating the first and second chambers with the first valve in the closed configuration, the polymeric material dissolving and becoming a solute in the fluid in response to exposure to the bioagent, wherein the polymeric material comprises peptide sequences to serve as recognition elements for the bioagent to be detected;
- a first detection structure disposed in the second chamber, the first detection structure generating a predetermined signal in response exposure to the fluid, wherein the first detection structure includes a microcapacitor having first and second terminals for connecting the first detection structure to a signal detection circuit.

10. The device of claim 9 wherein the body further defines a channel extending between the first and second chamber, the channel having an input communicating with the first chamber and an output communication with the second chamber and wherein the first valve overlaps the input to the channel.

11. The device of claim 9 wherein the second chamber accommodates the flow of fluid therein with the valve in the open configuration and wherein the microcapacitor has a first capacitance in the absence of fluid in the second chamber and a second capacitance with the fluid in the second chamber.

12. The device of claim 9 wherein the body defines a third chamber and wherein the device further comprises:
- a second valve disposed in the body, the valve having a first closed configuration wherein the first and third chambers are isolated and a second open configuration wherein the first and third chambers communicate; and
- a second detection structure disposed in the second chamber, the second detection structure generating a predetermined signal in response exposure to the fluid.

13. The device of claim 12 wherein the second valve is formed from a second polymeric material that isolates the first and third chambers, the second polymeric material dissolving in response to exposure to a second bioagent.

14. The device of claim 12 wherein the first valve opens a first predetermined time period after exposure to the bioagent and the second valve opens a second predetermined time period after exposure to the bioagent and wherein the first predetermined time period is less than the second predetermined time period.

15. The device of claim 12 wherein the first and second detection structures are connected in parallel.

16. A method of detecting the presence of a bioagent in a fluid, comprising:

passing the fluid into a body defining first and second chambers, the first and second chambers being isolated from each other by a first valve formed from a polymeric material, wherein the polymeric material comprises peptide sequences to serve as recognition elements for the bioagent to be detected;

dissolving the polymeric material into a solute in the fluid in response to exposure to the bioagent in the fluid so as to allow fluid to flow into the second chamber;

generating a signal in response to the presence of fluid in the second chamber, wherein the step of generating a signal includes the additional steps of:

providing a microcapacitor having an initial capacitance in the second chamber;

varying the capacitance of the microcapacitor in response to the presence of fluid in the second chamber; and detecting the change in capacitance.

17. The method of claim 16 comprising the additional steps of:

providing a third chamber in the body;

opening a second valve in response to a second bioagent in the fluid so as to allow fluid to flow into the third chamber; and generating a second signal in response to the presence of fluid in the third chamber.

18. The method of claim 16 comprising the additional steps of:

providing a third chamber in the body;

opening a second valve in response to the bioagent in the fluid so as to allow fluid to flow into the third chamber; and varying the signal in response to the presence of fluid in the third chamber.

19. The method of claim 18 wherein the polymeric material of the first valve is a first polymeric material that isolates the first and second chambers, the first polymeric material dissolving in a first predetermined time period in response to exposure to the bioagent and wherein the second valve is formed from a second polymeric material that isolates the first and third chambers, the second polymeric material dissolving in a second predetermined time period in response to exposure to the bioagent.

20. The method of claim 18 wherein the first and second valves open sequentially in response to exposure to the bioagent in the fluid.

* * * * *